United States Patent [19]

Nicolson et al.

[11] Patent Number: 5,078,798

[45] Date of Patent: Jan. 7, 1992

[54] BUOYANCY MEDIATED CONTROL OF CATALYTIC REACTION

[75] Inventors: Paul Nicolson, Dunwoody; Kenneth R. Seamons, Marietta; Fu-Pao Tsao, Lawrenceville, all of Ga.

[73] Assignee: Ciba-Geigy Corporation, Ardsley, N.Y.

[21] Appl. No.: 458,123

[22] Filed: Dec. 28, 1989

[51] Int. Cl.$^5$ .......................... B08B 3/04; B08B 3/08; B08B 7/00

[52] U.S. Cl. ........................................ 134/7; 134/30; 134/42; 502/7; 502/159; 422/177

[58] Field of Search ............... 134/42, 7, 30; 422/177; 502/159, 7

[56] References Cited

U.S. PATENT DOCUMENTS 3,912,451  10/1975  Gaglia ..................................... 134/42
4,670,178  6/1987  Huth et al. .................. 252/174.12 X
4,748,992  6/1988  Giefer .............................. 252/106 X

FOREIGN PATENT DOCUMENTS 2309240  12/1976  France .
7407482  12/1974  Netherlands ........................... 134/42

*Primary Examiner*—Theodore Morris
*Assistant Examiner*—Zeinab El-Arini
*Attorney, Agent, or Firm*—Wenderoth, Lind & Ponack

[57] ABSTRACT

A method of carrying out a reaction in a solution catalytically comprising contacting a solid catalytically active material and a solution in which a catalytic reaction is to be carried out wherein the catalytic reaction yields a gas which adheres to the catalyst particles such that as the reaction is substantially complete in the immediate environment of the catalyst, the catalyst migrates to a reactant richer portion.

29 Claims, 2 Drawing Sheets

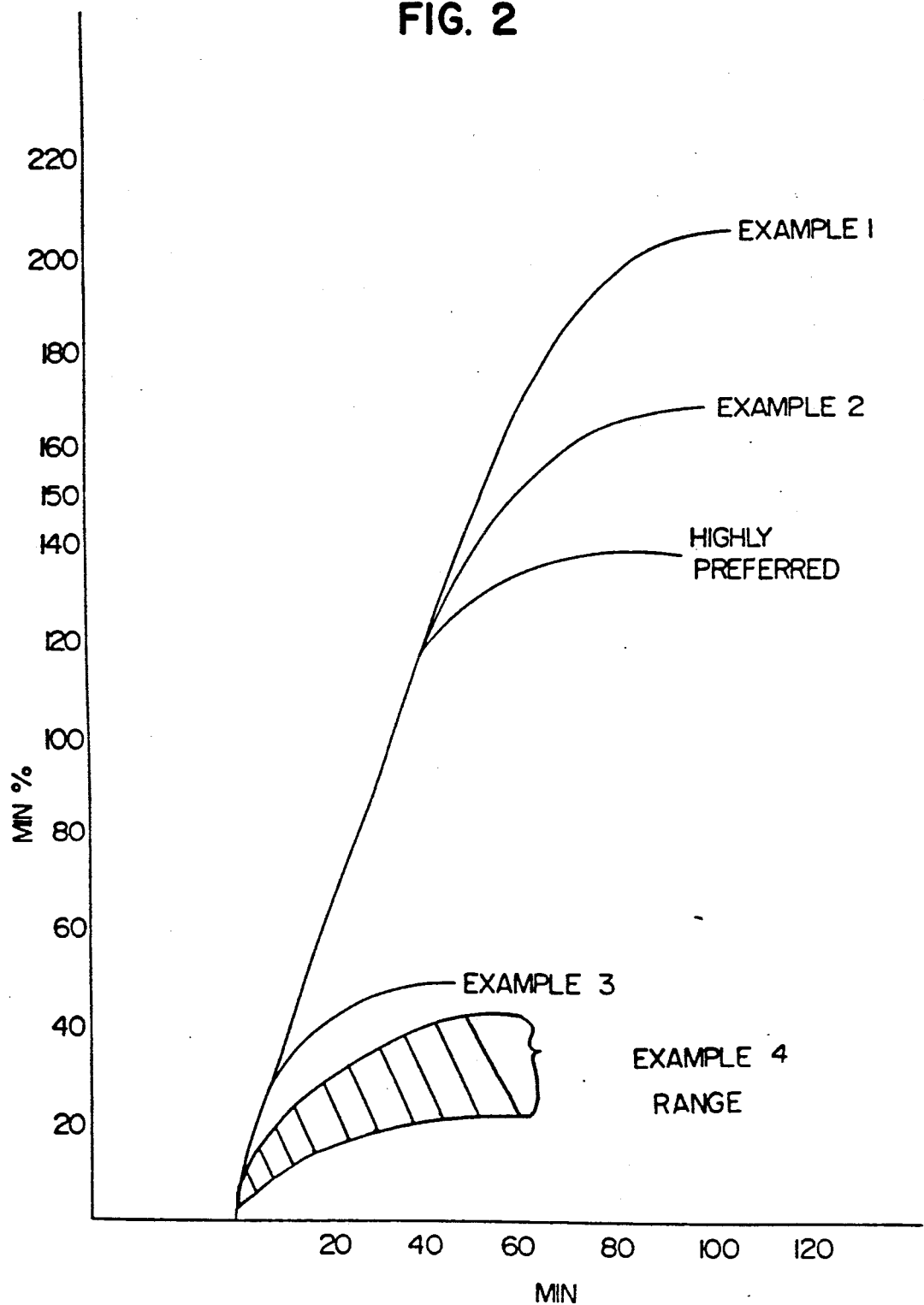

BUOYANCY MEDIATED CONTROL OF CATALYTIC REACTION

FIELD OF THE INVENTION

The invention generally relates to catalytic reactions where the reaction is to proceed over a period of time but not in a homogeneous manner. It especially relates to catalytic breakdown of hydrogen peroxide.

BACKGROUND OF THE INVENTION

In the contact lens field, catalytic decomposition of disinfectant is an important process where the disinfectant must be totally removed from the article being disinfected and washing with large volumes of water or other solvent is not a viable alternative. In many of these settings, there is insufficient user attention to details of how long the disinfectant must remain in contact with the article being disinfected, a failure to adhere to the regimen because of its complexity, or simply a desire to reduce procedural steps.

Some of these problems have been encountered with catalytic decomposition of hydrogen peroxide disinfection systems. For example, a commercially available disinfection system using hydrogen peroxide fixes a platinum catalyst to the bottom of a disinfection container containing hydrogen peroxide simultaneously with the introduction of contact lenses for disinfection. The catalyst quickly decomposes the hydrogen peroxide in the immediate vicinity of the catalyst generating oxygen which bubbles up through the solution recreating a nearly homogeneous, although slightly less concentrated, peroxide solution. As a result, there is uniform depletion of the disinfectant hydrogen peroxide within the system. While this is adequate for a number of disinfecting purposes, for some others it is not. Clearly, longer transition time in higher disinfectant concentrations would insure better compliance and less chance of product failure when used with more heavily contaminated materials needing disinfection.

It is an object of the invention to provide a method of carrying out a catalytic reaction in a controlled manner allowing for greater transition times of a substance in the reactant mixture prior to the catalytic reaction occurring to a significant degree in the vicinity of that substance.

It is another object of the invention to provide a contact lens hydrogen peroxide disinfection system and method which avoids the aforementioned problems and/or difficulties.

SUMMARY OF THE INVENTION

Surprisingly, the foregoing objects and others can be achieved by carrying out a catalytic reaction (a) in a liquid which generates a gas that gives the catalytic particle sufficient buoyancy to rise to the surface of the liquid phase or (b) in a liquid wherein the reaction product solution is of a significantly different density than and substantially non-miscible with the reactant solution and the catalytic particle is of appropriate density that at least a portion thereof tends to remain in contact with the reactant solution portion and of sufficient buoyancy so as to be at or near the reactant solution/reaction product solution interface.

BRIEF DESCRIPTION OF THE DRAWINGS

FIG. 2 is a graph showing the decomposition profile of hydrogen peroxide as expressed in terms of the cumulative area under the peroxide % vs. time curve.

DETAILED DESCRIPTION OF THE INVENTION

Figure 1:
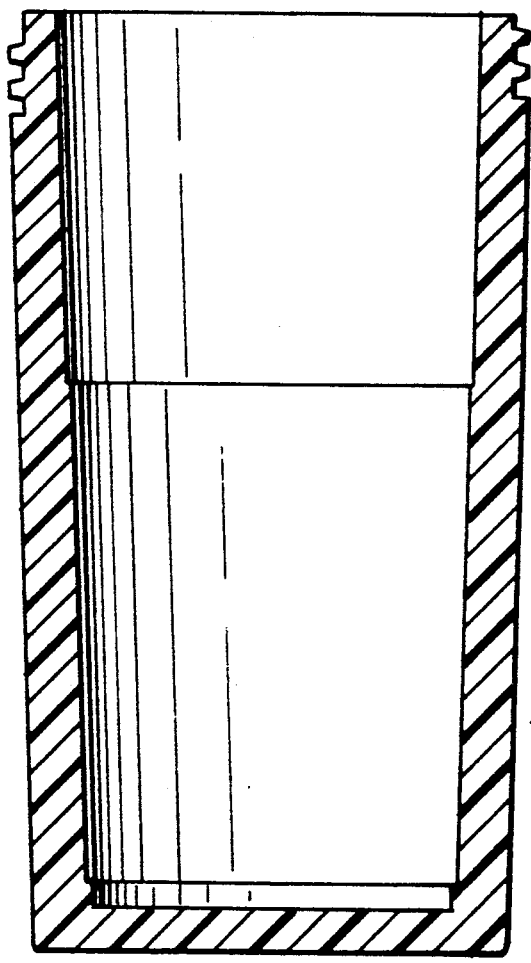
FIG. 1 is a sample cup used to measure the percentage of peroxide in the vicinity of a contact lens to be sterilized according to the method of the present invention.

Buoyancy controlled catalytic reactions fall into two primary types of reactions. First are those reactions which generate a gas. The gas bubbles adhere to the surface of the catalyst particle creating a buoyant particle. The buoyant particle rises to the surface where the gas bubble escapes to the gas phase over the liquid reaction medium. Upon losing the gas bubbles, the catalyst loses buoyancy and begins to descend until it again contacts liquid containing reactants so that further buoyant gas bubbles can be generated. This bobbing action, is therefore confined to the uppermost layers of the reactant solution and the reaction product solution, leaving the lower portion of the reactant solution substantially undisturbed for a significant portion of time.

Depending on the speed with which a particular reaction is intended to take place, the buoyancy of the catalyst can be altered by coating a carrier or substrate particle of particular density with varying amounts of catalyst. The less dense the particle, the more it will extend the reaction time as such a particle will be confined more to the uppermost reactant solution portions and reaction product solution. Similarly, the greater the amount of catalyst at the particle surface, the more the particle will find itself in the uppermost reactant solution and reaction product solution. Particle shape also plays a part in reaction rate control. Spherical particles will tend to lose their gas bubble lifters quicker than other shapes, yet they move more easily through the liquid solutions than other particle shapes. Finally, particle size is important in control of the reaction rate in relation to changes in particle weight vs. particle surface area. The greater the weight, the more buoyant force needed from gas bubbles; if surface area does not increase at least as rapidly, then the particle will reside for a greater time in the reactant solution area and thereby speed up the reaction more so than otherwise. Counterbalancing this is the fact that the greater the catalyst surface area, the faster the reaction, and the shorter the residence time of the article to be disinfected in the disinfectant.

In the second type of buoyancy controlled catalytic reaction, the catalytic particle resides, due to its density, at or near the reactant solution/reaction product solution interface, at least part of it tending to remain in contact with the reactant solution. If the reaction product solution is less dense than the reactant solution, then the reaction proceeds substantially from top to bottom and the catalytic particles are designed to be slightly less dense than the reactant solution (i.e. between the reaction product and reactant solution densities). If the reaction product solution is more dense than the reactant solution, then the reaction proceeds from bottom to top and the catalytic particle is designed to be slightly more dense than the reactant solution. In either event, the catalytic particle must return to contact reactant solution if the reaction is to continue to proceed. In either case, if the reaction product adheres to the catalyst for sufficient time to drive the catalyst toward the reaction product solution, the catalyst particles may also be of the same density as the reactant solution.

Typical catalytic reactions of the first (i.e. gas) type include, but are not limited to, hydrogen peroxide solution with peroxidase, catalase, or transition metals such as platinum, palladium, etc. and compounds thereof such as iron oxide, manganese oxide or $TiO_2$ catalyst particles.

Typical catalytic particles can be prepared from refractory, plastics, fiber, etc. particles having an appropriate configuration which are then overcoated or impregnated with catalyst, such as platinum, catalase, etc.

Convenient particle shapes include but are not limited to discs, plates, spheres, stars, "donuts", wafers, tubes, rods and strips. Essentially any particle shape will suffice.

Suitable particle sizes for spheres are particles with diameters of from about 0.5 mm up to about 5 cm, preferably about 1 mm to about 2 cm, more preferably about 3 mm to about 1 cm, most preferably about 4 mm to about 8 mm. Suitable, although not limiting for a plate or disc, or wafer shape is 1 cm $\times$ 2 cm $\times$ 0.02 cm. Appropriate size limits for other shapes can readily be inferred by those of ordinary skill. To balance particle size and surface area to the desired ratio, one may use multiple smaller sized particles, for example 3 particles of 1 mm diameter each instead of one particle of equivalent weight or surface area.

For the second embodiment of the invention (that in which gas need not be generated), the catalyst particle does not vary far from the reactant solution/reaction product solution interface, and particle movement considerations are less importment. Hence, there is greater flexibility in terms of catalyst shape and more concern with appropriate density for the particle. While it is expected that there is going to be little if any "bobbing" action, such movement is not precluded. In fact, to the extent the reaction product generated by the catalytic reaction adheres to the catalyst, there may be some significant positive or negative buoyant effect (depending upon whether the product solution is less dense or more dense than the reactant solution). Beyond these concerns, the catalytic particles for use in the first embodiment are also suitable for use in the second embodiment of the present invention.

The gas producing reaction is most preferably the degeneration of hydrogen peroxide to water and oxygen gas. In the gas generating reactions, preferable particle shapes are stars, plates, discs, wafers, spheres, rods, strips and donuts; more preferably, spheres, donuts, rods, plates, discs, and wafers; most preferably plates, discs, wafers, and spheres.

The particular density of the catalytic particle is dependent upon how fast and far the particle is to penetrate back into the reactant solution phase. For a given shape, the greater the density, the longer it will take to generate sufficient buoyant force to lift it out of the reactant solution phase (in gas generating systems and those where reaction products are less dense than reactants), yet as the surface area increases relative to weight, the less time the particle will spend in the reactant solution.

For the hydrogen peroxide/oxygen gas system, the preferred parameters are density of the catalyst particle of from 1.05 to about 1.30, preferably from about 1.10 to about 1.20, most preferably from about 1.12 to about 1.18; surface area of the particle of about 0.008 to about 75 $cm^2$, preferably about 0.03 $cm^2$ to about 13 $cm^2$, more preferably about 0.2 $cm^2$ to about 5 $cm^2$, most preferably about 0.3 $cm^2$ to about 3.2 $cm^2$; and surface area/weight ratio of the particle of from about 0.85 to about 116, preferably about 1.15 to about 54.5, most preferably about 2.95 to about 11.3.

The surface may be anything from smooth to rough with rough surfaces provided a larger effective surface area than the same sized and shaped particle of smooth morphology. The rough morphology will also allow for greater "lifter" adherence.

The hydrogen peroxide/oxygen gas system of the invention has a decomposition profile, such that total area under the % peroxide (in the vicinity of the lens) vs. time is in excess of 47%min, preferably in excess of 50%min, more preferably greater than about 75%min, still more preferably more than about 100%min, even more preferably in excess of about 120%min, and most preferably more than about 140%min, when using a current commercially available AO ® Sept cup, approximately 3% peroxide, and sampling the peroxide in the vicinity of the lens with the lens placed standing on edge at the bottom of the cup and the cup filled to the indicated line. A sample cup used in these tests for conformity with the decomposition profile is shown in FIG. 1.

The cumulative area under the peroxide % vs. time curve is shown in FIG. 2 for three examples as well as the prior art system where the catalytic material is in a fixed position at the bottom of the solution.

This graph is arrived at by first calculating the area under a curve in which the percentage of hydrogen peroxide as the ordinate is plotted against time in minutes, as the abscissa. In such case, the area under the curve is integrated or calculated at various time intervals to determine the cumulative area in terms of % minutes. This area in turn is plotted against time to measure the rate at which the hydrogen peroxide decomposes with time. Thus, the higher the % minutes or cumulative area under the above-mentioned curve, the lower the decomposition rate of the hydrogen peroxide.

Furthermore, in the hydrogen peroxide/oxygen gas system, residual peroxide content should be with ocularly tolerable levels preferably within less than about 8 hours, preferably less than about 6 hours, more preferably less than about 4 hours, still more preferably less than about 2 hours, most preferably less than about 90 minutes.

Still further the peroxide content should be, at the sample point, at or in excess of a disinfectantly effective concentration (i.e. at or more than 1%) for at least 15 minutes, preferably at least 20 minutes, more preferably at least 30 minutes after decomposition of the approximately 3% hydrogen peroxide solution has begun. When starting with a greater concentration of peroxide, this time period can be shortened provided the % time value for the time the peroxide concentration exceeds 35, preferably 40, in the first 15 minutes of decomposition and exceeds 40, preferably 50, more preferably 55 in the first 20 minutes of decomposition and exceeds 45, preferably 50, more preferably 60, most preferably 80, in the first 30 minutes of decomposition.

In the second embodiment of the invention, similar considerations apply with appropriate concern for whether the reactant solution is more or less dense than the reaction product solution.

The carrier or substrate for the catalyst can be any material that is resistant to the chemical activity of hydrogen peroxide, the catalyst being used, and oxygen gas. Most preferable for the substrate is a synthetic plastic. Of these, the material of choice is a polycarbonate, especially polycarbonate mixed with acrylate butadiene styrene.

The substrate can be prepared in its desired size and shape by well known techniques, including: extrusion, molding, cutting, chipping, milling, lathing, and/or grinding, and coated with catalyst by spraying, dipping, fluidized bed techniques, vapor phase deposition, or any other suitable known coating technique so long as the catalyst is not destroyed in the process.

The invention further relates to a buoyancy controlled catalytic reaction vessel having a liquid reactant medium container, means for input of said liquid reactant medium and at least one catalytic particle and means for outflow of the product resulting from the catalytic reaction, and optionally means for selectively removing the reaction product or the catalytic particle from the vessel.

In the embodiment designed to accommodate hydrogen peroxide disinfection of contact lenses on a non-continuous basis, the vessel comprises a vial having an opening at one end thereof, a cap for sealing said vial from the environment, a release valve in said cap or vial walls or cap-vial junction to release gas pressure buildup, and a means for restricting the position of contact lenses undergoing disinfection at a position distal to the opening of said vial. This embodiment further may optionally contain a sleeve or webb which allows movement of catalyst particles therethrough in the vertical direction between the opening and the portion of the vial distal thereto.

The instant invention will be more fully understood with reference to the following examples which illustrate but do not limit the instant invention.

Test procedures were as follows:

Commercial AO ® Sept cups were filled to the premarked line with about 3.3% hydrogen peroxide (about 9 mls). The system, for peroxide determination, was left open, without the cap or stem inserted. A 50 ul sample was taken and assayed. The catalytic particles used for the invention were placed into the container. Additional 50 ul samples were withdrawn at the specified times from the bottom of the cup (approximately 22 mm from the upper surface of the solution). The typical cup used is shown in FIG. 1.

EXAMPLE 1

6 of 6 mm diameter (pre-coating size) pt coated balls (polycarbonate mixed with acrylate butadiene styrene, pre-coating density is 1.11 g/ml) were put in AO ® Sept cups, filled with AO ® Sept solution (3-3.5% $H_2O_2$ with phosphate buffered saline) up to the line, and the concentration of $H_2O_2$ 23-25 mm from the upper surface measured during the interval time. The results are listed on the following table. The (% peroxide.min) vs. min curve is shown in FIG. 2.

EXAMPLE 2

The procedure of Example 1 was repeated except that 4 of 8 mm diameter (pre-coating size) balls (Noryl, pre-coating density is 1.06 g/ml) were employed. The results are listed on the following table. The (% peroxide.min) vs. min curve is shown in FIG. 2.

EXAMPLE 3

The procedure of Example 1 was repeated except that 6 of 4 mm diameter (pre-coating size) balls (polycarbonate, pre-coating density is 1.19 g/ml) were employed. The results are listed on the following table. The (% peroxide.min) vs. min curve is shown in FIG. 2.

EXAMPLE 4

The commercially available AO ® Sept system was used, with the same concentration of peroxide, in 6 runs. The (% peroxide.min) vs. min curve is shown in FIG. 2. Samples were taken as close as possible to the same position as in Examples 1-3. Due to the fact that the catalyst in this example is held at the bottom and the oxygen bubbles up through the entire range, sufficient mixing is present to eliminate any theoretical difference present due to slightly different sampling positions.

The concentration of hydrogen peroxide (%) at the time of interval and after 6 hrs. (ppm).

| Time (min) | Examples | | |
|---|---|---|---|
| | 1 | 2 | 3 |
| 0 | 3.3 (%) | 3.3 (%) | 3.3 (%) |
| 5 | 3.0 | 3.1 | 3.1 |
| 7 | 3.1 | 3.1 | 3.0 |
| 10 | 3.1 | 3.2 | 2.9 |
| 15 | 3.0 | 2.8 | 1.8 |
| 20 | 2.7 | 2.6 | 1.1 |
| 25 | 3.0 | 2.4 | 0.4 |
| 30 | 2.9 | 2.5 | 0.3 |
| 40 | 2.8 | 2.5 | 0.2 |
| 50 | 2.3 | 1.6 | 0.0 |
| 60 | 2.0 | 1.5 | — |
| 75 | 1.7 | 1.2 | — |
| 90 | 0.3 | 0.2 | — |
| 105 | 0.0 | 0.0 | — |
| 120 | — | — | — |
| 6 (hrs) | 60,61 (ppm) | 4,5 (ppm) | 2,3 (ppm) |

We claim:

1. A method of buoyantly controlling a catalytic reaction comprising contacting a liquid reaction medium and a particulate catalyst capable of converting said liquid reactant medium into a reaction product, said particulate catalyst having a density such that it (a) remains substantially at the reactant medium/reaction product interface; (b) it sinks into the reactant medium but generates a positive buoyant force which adheres for a time to said particle driving said particle toward the reactant solution surface or total solution surface, the reaction product thereof being as dense or less dense than said reactant medium; or (c) it rises into the reactant medium but generates a negative buoyant force which adheres for a time to said particle driving it toward the reaction product solution therefrom, said reaction product being more dense than said reactant solution; and upon losing said buoyant force, attempts to return to its pre-buoyant force position until a new buoyant force is generated.

2. The method of claim 1 wherein said catalytic reaction is the catalytic decomposition of hydrogen peroxide.

3. The method of claim 3 wherein said catalyst is selected from transition metals and compounds thereof and enzymes.

4. The method of claim 3 wherein said enzymes are selected from peroxidase and catalase.

5. The method of claim 4 wherein said transition metal is selected from platinum, palladium, iron, manganese, and titanium, and said transition metal compounds are the oxides of said transition metals.

6. The method of claim 3 wherein said catalyst is selected from platinum and catalase.

7. The method of claim 1 wherein said catalytic reaction is the catalytic decomposition of aqueous hydrogen peroxide and said catalyst is present as a shaped substrate having said catalyst coated thereon or impregnated therewith, said substrate impregnated with catalyst having sufficient porosity to aqueous hydrogen peroxide to permit said catalytic reaction to occur and allow escape of reaction product from the internal portions of said substrate.

8. The method of claim 7 wherein said substrate is a polymer of natural or synthetic origin resistant to the chemical effects of reactant, reaction product and catalyst.

9. The method of claim 8 wherein said substrate is a synthetic polymer selected from polycarbonate alone or in admixture with acrylate butadiene styrene or with noryl.

10. The method of claim 9 wherein said substrate is polycarbonate.

11. The method of claim 9 wherein said substrate is coated with said catalyst.

12. The method of claim 1 wherein said catalyst is pure catalyst, catalyst coated substrate, or catalyst impregnated substrate, and has a shape selected from a plate, a disc, a wafer, a sphere, a rod, a strip, a donut, an egg shape, a tear drop, a star, and gear shape;
   a density of from about 1.05 to about 1.30;
   a surface area of about 0.2 cm² to about 5 cm²; and
   and a weight/surface area ratio of about 0.85 to about 116.

13. The method of claim 12 wherein the catalyst is present as a coating on a substrate, the catalytic reaction is the catalytic decomposition of hydrogen peroxide and the catalyst is platinum or catalase.

14. The method of claim 14 wherein said catalyst coated substrate has a sphere shape.

15. The method of claim 13 wherein said catalyst coated substrate has a density of about 1.12 to about 1.18.

16. The method of claim 14 wherein said catalyst coated substrate has a surface area of about 0.3 cm² to about 3.2 cm².

17. The method of claim 13 wherein said catalyst coated substrate has a weight to surface area ratio of about 2.95 to about 11.3.

18. The method of claim 3 wherein said hydrogen peroxide content remain present in a disinfectingly effective concentration in the vicinity of an article to be disinfected therein for at least 15 minutes after said catalytic reaction has begun.

19. The method of claim 18 wherein said article to be disinfected therein is a contact lens.

20. A method of decomposing a hydrogen peroxide solution comprising contacting said solution with freely moving catalytic particles which upon making said contact generate sufficiently adherent oxygen bubbles to give said particles a buoyant force whereby said particles are lifted toward the surface of said solution until said oxygen bubbles are lost whereupon said particle sinks through said solution until sufficient buoyant force is generated by further catalytic decomposition and generation of further adherent oxygen bubbles such that a non-homogeneous decomposition takes place beginning near the top of the peroxide solution and ending at the bottom thereof.

21. The method of claim 20 wherein said peroxide solution starts at a concentration of about 3.0 to about 3.5% hydrogen peroxide.

22. The method of claim 20 wherein said hydrogen peroxide decomposition is substantially complete such that said solution is ocularly compatible within a first time period of about 8 hours.

23. The method of claim 22 wherein said time period is within 6 hours.

24. The method of claim 22 wherein said time period is within about 4 hours.

25. The method of claim 22 wherein said time period is within about 2 hours.

26. The method of claim 22 wherein said time period is within about 90 minutes.

27. The method of claim 20 wherein said hydrogen peroxide concentration remains in excess of 1% at the bottom of the solution for a second time period of at least 15 minutes.

28. The method of claim 27 wherein said second time period is at least b 20 minutes.

29. The method of claim 27 wherein said second time period is at least 30 minutes.

* * * * *